United States Patent
Brock-Fisher

(10) Patent No.: US 6,533,727 B1
(45) Date of Patent: Mar. 18, 2003

(54) ULTRASONIC SYSTEM AND METHOD EMPLOYING NON-INTEGER HARMONIC ECHO SIGNALS FOR IMAGING

(75) Inventor: George A Brock-Fisher, Andover, MA (US)

(73) Assignee: Koninklijke Phillips Electronics N.V., Eindhoven (NL)

(*) Notice: Subject to any disclaimer, the term of this patent is extended or adjusted under 35 U.S.C. 154(b) by 0 days.

(21) Appl. No.: 09/505,453

(22) Filed: Feb. 11, 2000

(51) Int. Cl.$^7$ ................................................ A61B 8/00
(52) U.S. Cl. ........................................ 600/458; 424/9.5
(58) Field of Search ................................ 600/437–438, 600/440–472

(56) References Cited

U.S. PATENT DOCUMENTS

| | | | | |
|---|---|---|---|---|
| 5,410,516 A | * | 4/1995 | Uhlendorf et al. | 367/7 |
| 5,577,505 A | * | 11/1996 | Brock-Fisher et al. | 600/458 |
| 5,833,613 A | * | 11/1998 | Averkiou et al. | 600/440 |
| 5,879,303 A | * | 3/1999 | Averkiou et al. | 600/447 |
| 6,102,858 A | * | 8/2000 | Hatfield et al. | 600/443 |
| 6,213,951 B1 | * | 4/2001 | Krishnan et al. | 600/458 |
| 6,284,280 B1 | * | 9/2001 | Weitschies et al. | 424/489 |
| 6,302,845 B2 | * | 10/2001 | Shi et al. | 600/438 |

* cited by examiner

Primary Examiner—Francis J. Jaworski
Assistant Examiner—William C Jung
(74) Attorney, Agent, or Firm—John Vodopia

(57) ABSTRACT

The method of the invention controls an ultrasound system to image a microbubble contrast agent in a region of fluid flow and/or a region of tissue that is perfused by blood or other fluid. A transducer transmits ultrasound acoustic signals having a fundamental frequency f and receives echoes resulting from interaction of the ultrasound signals with both tissue and the microbubble contrast agent. A transmitter controls the transducer to transmit ultrasound signals at a sufficient power level to destroy the microbubble contrast agent. A receiver processes the echoes and selectively extracts signal components that exhibit a noninteger multiple of the fundamental frequency f of the transmitted acoustic signal. The system then produces images, principally from signal components including those that exhibit the noninteger multiple of the fundamental frequency f.

3 Claims, 2 Drawing Sheets

ULTRASONIC SYSTEM AND METHOD EMPLOYING NON-INTEGER HARMONIC ECHO SIGNALS FOR IMAGING

FIELD OF THE INVENTION

This invention relates to ultrasonic imaging of perfusion of an anatomical region and, more particularly, to a method for enabling imaging of a contrast agent with reduced tissue clutter.

BACKGROUND OF THE INVENTION

Current ultrasonic imaging systems make use of contrast agents in circulation to enhance ultrasound returns. Contrast agents are substances which strongly interact with ultrasound waves and return echoes which may be clearly distinguished from those returned by blood and tissue. Microbubbles are currently employed as a contrast agent and provide a non-linear behavior in certain acoustic fields. Such behavior is readily detectable by use of known algorithms. Microbubble contrast agents are useful for imaging of the body's vascular system and are injectable through the veins and arteries. They are subsequently filtered from the blood stream by the lungs, kidneys and liver.

Microbubble contrast agents generally comprise coated gas bubbles that are stable in the body for a significant period of time. The coating shells serve to protect the gas from diffusion into the blood stream. At moderately high ultrasound pressure amplitudes, the shells of the microbubbles can be caused to rupture, freeing the internal gas and substantially eliminating the detectability thereof by incident ultrasound waves.

U.S. Pat. No. 5,410,516 to Uhlendorf et al. describes an ultrasound system that produces images from echo returns from a microbubble contrast agent. The echo signals that are used for imaging are those that exhibit harmonic and subharmonic relationships to the fundamental transmission frequency.

U.S. Pat. No. 5,833,613 to Averkiou et al. discloses an ultrasound method for imaging of contrast agents. In one embodiment, a rate of re-perfusion of an anatomical region is accomplished by initially destroying the contrast agent within the region, and then subsequently imaging the region to determine the rate of re-insertion of the contrast agent. The Averkiou et al. method of indicating the rate of re-perfusion utilizes plotted curves that indicate echo returns from interrogating ultrasound beams. Initially, Averkiou et al. transmit high energy ultrasound pulses to destroy the microbubbles in the region to be imaged. A short time later, lower energy, imaging, ultrasound pulses are transmitted again, the echoes received and imaged to measure the degree of microbubble re-infusion by, for example, counting or integrating the pixels in the area which show re-infused microbubbles. The measure of the number of re-infused microbubbles in the region is plotted in curve format. Non-destructive pulses can thereafter be repetitively transmitted and echoes received and plotted as a sequence of points to indicate the rate of re-perfusion.

U.S. Pat. No. 5,879,303 to Averkiou et al. discloses still another ultrasound method for imaging of contrast agents. In this patent, a programmable digital filter is used to pass harmonic echo components to the exclusion of fundamental frequency components of the transmitted signal. The system uses decorrelated replicas of the harmonic signal that are then combined and used for imaging. To produce an image in the presence of depth dependent attenuation of high frequency echo signals, both fundamental and harmonic signals are processed and used to produce an image blended from components of both the fundamental and harmonic signals.

U.S. Pat. No. 5,577,505 to Brock-Fisher et al discloses an ultrasound method for imaging of contrast agents that achieves increased sensitivity to non-linear responses, particularly second harmonic responses under multiple excitation levels. In particular, the responses gathered from multiple echoes are gain corrected in an amount corresponding to the difference in excitation levels and are then subtracted. The subtraction removes most of the linear tissue response and what remains is the non-linear response from contrast agent.

It is known that the contrast ratio of ultrasound images is limited by a second harmonic response that results from interaction between tissue and incident ultrasound acoustic energy. Such harmonic response is caused by non-linear propagation effects which give rise to second harmonic energy in the transmitted acoustic signal. Further, when contrast agent is destroyed, its acoustic response ceases to be constrained by frequency regions around the transmit frequency or harmonics thereof. More specifically, when a microbubble contrast agent is destroyed, its acoustic response becomes broadband and exhibits energy in a broad spectrum of frequencies.

There is a need for improved ultrasound images from contrast agent. Further, harmonic tissue response in such images should be reduced to enhance the contrast of the contrast agent echo returns so as to improve images that are derived therefrom.

SUMMARY OF THE INVENTION

The method of the invention controls an ultrasound system to image a microbubble contrast agent in a region of fluid flow and/or a region of tissue that is perfused by blood or other fluid. A transducer transmits ultrasound acoustic signals having a fundamental frequency f and receives echoes resulting from interaction of the ultrasound signals with both tissue and the microbubble contrast agent. A transmitter controls the transducer to transmit ultrasound signals at a sufficient power level to destroy the microbubble contrast agent. A receiver processes the echoes and selectively extracts signal components that exhibit a noninteger multiple of the fundamental frequency f of the transmitted acoustic signal. The system then produces images, principally from signal components including those that exhibit the noninteger multiple of the fundamental frequency f.

DETAILED DESCRIPTION OF THE PREFERRED EMBODIMENT

Figure 1:
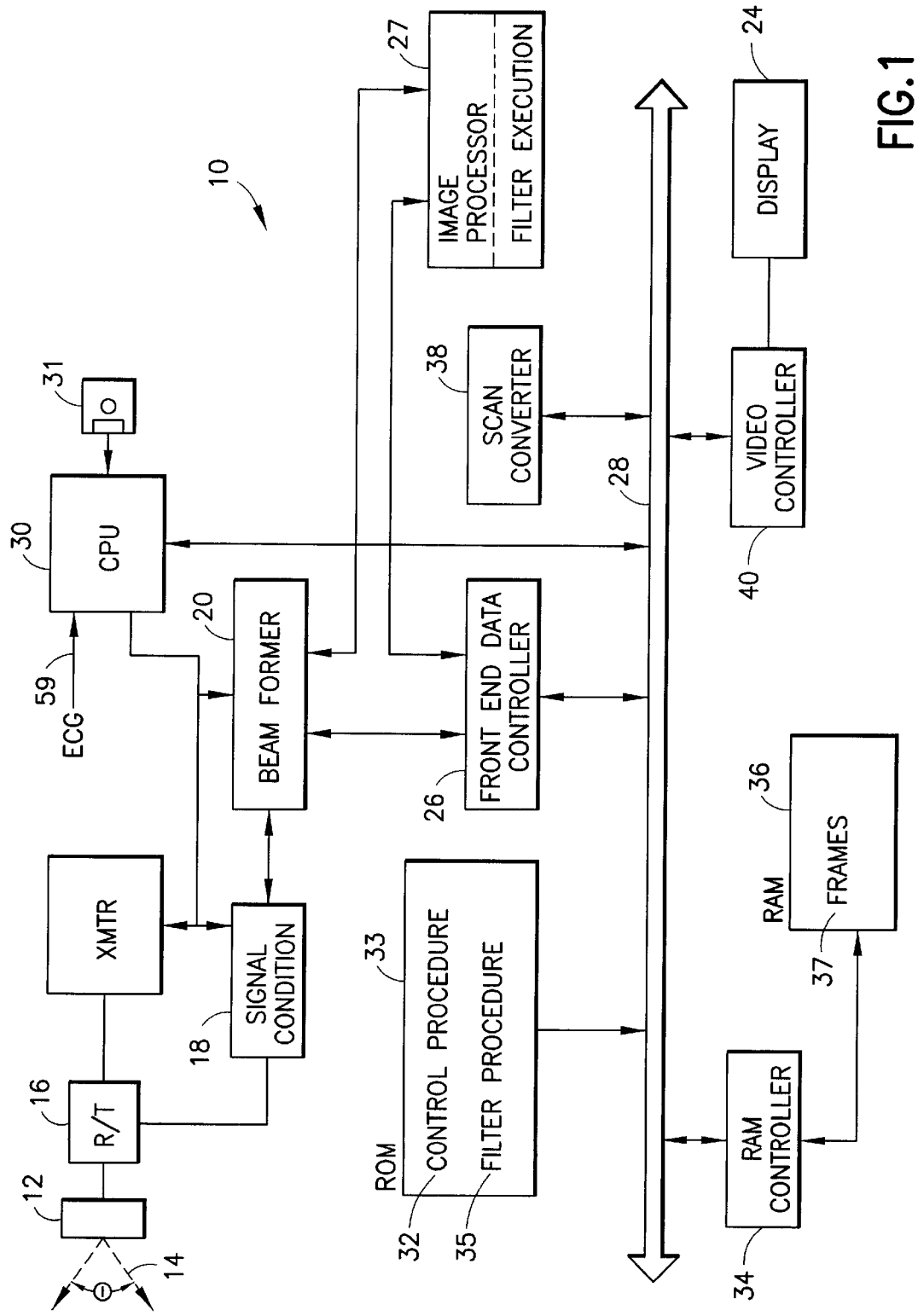
FIG. 1 is a high-level block diagram of an ultrasound imaging system incorporating the invention.

During the following description of the invention, it will be assumed that ultrasound system 10 (see FIG. 1) has been adjusted so as to image a region of interest (ROI) within a patient's anatomy. Prior to a scan of the ROI, a contrast agent is introduced into the blood stream or other fluid. A high energy, narrow bandwidth ultrasound acoustic signal is then transmitted so as to destroy the contrast agent within the ROI, or at least, within a portion of the ROI that is to be imaged.

The echo signals from the ROI are received and processed through a filter function that preferentially passes signals lying in a bandwidth that encompasses a noninteger multiple of the fundamental frequency of the transmitted acoustic signal. Such bandwidth includes broadband echo signal returns from the contrast agent, to the significant exclusion of frequencies at the fundamental transmit frequency, and integer harmonics thereof.

The narrow bandwidth of the transmitted acoustic signal reduces the bandwidth of the second harmonic tissue response, causing an intermediate frequency band between the fundamental and the second harmonic to be relatively free of tissue second harmonic response. Additionally, intermediate frequency bands between successively higher integer multiples of the fundamental frequency will also be relatively free of higher integer harmonic tissue responses.

By causing the transmit acoustic signal to exhibit a sufficiently high level of power to destroy the contrast agent, a relatively broadband echo signal results from the destruction event, with a significant energy component in the aforesaid intermediate frequency band(s). By subjecting the received echoes signals to selective filtering to recover the signals in the intermediate band(s) and using those signal components to produce images, a higher contrast ratio is obtained for signals from contrast agent to signals from tissue Referring now to FIG. 1, ultrasound system 10 includes a transducer 12 that, in the known manner, scans an ultrasound beam 14 through a predetermined angle. Radio frequency acoustic echo signals are sensed by transducer 12 and are fed through a receive/transmit switch 16 to a signal conditioner 18 and, in turn, to a beamformer 20. Signal conditioner 18 receives the echo signals and conditions those signals by amplification and forming circuitry, prior to their being fed to beamformer 20. Within beamformer 20 and under control of front end data controller 26, the RF acoustic signals are converted to coherent "lines" of digital RF signal values in accordance with the echo signals from points along an azimuth of beam 14.

Beamformer 20 feeds the RF digital signal values to an image processor 27 that buffers each line, as received. After one or more lines of digital values have been accumulated by image processor 27, front-end data controller 26 dispatches a signal via a bus 28 to a central processing unit (CPU) 30. CPU 30 then executes a control procedure 32 (from ROM 33) that enables individual, asynchronous operation of each of the processing modules within ultrasound system 10.

CPU 30, via control procedure 32, causes image processor 27 to call filter procedure 35 from ROM 33. Filter procedure 35 is executed by image processor 27. The bandpass of filter procedure 35 is set to be centered at one or more noninteger multiples of the fundamental transmit frequency "f", preferably about 1.5 (f). Accordingly only a band of signal values distributed about 1.5 f are passed for further processing in accord with the invention.

Figure 2:
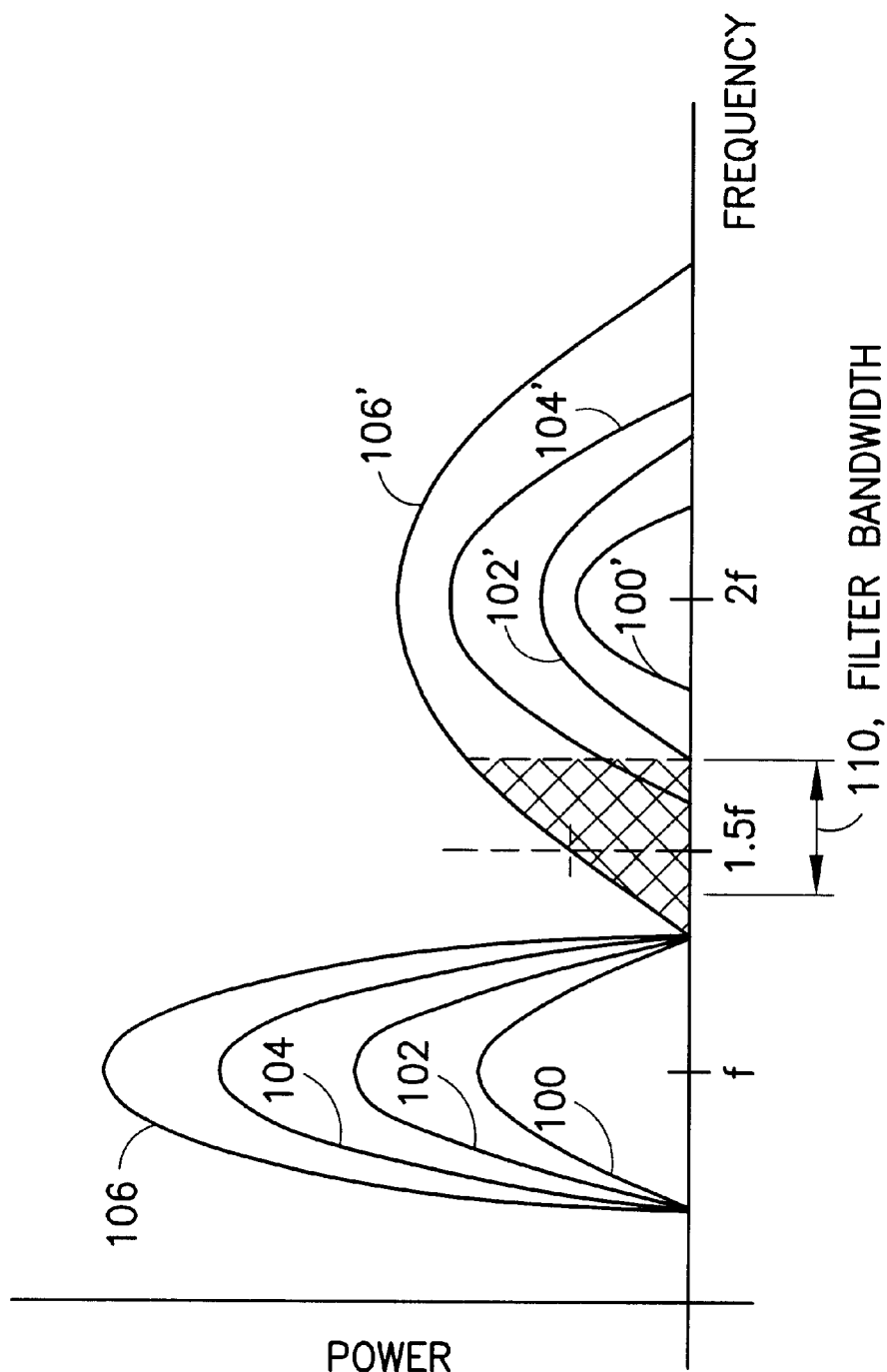
FIG. 2 a plot of transmit signal frequency power and receive signal second harmonic bandwidth versus power, also showing the bandwidth of a receive filter function.

Referring to FIG. 2, a plot of power versus frequency is shown that will enable a better understanding of the invention. Curves 100, 102, 104, and 106 represent succeedingly higher levels of transmit power versus bandwidth. Curves 100', 102', 104', and 106' represent the corresponding second harmonic echo signal magnitudes versus bandwidth. Each of curves 100', 102', 104', and 106' includes second harmonic returns from both contrast agent and tissue. However, at transmit power level 106, sufficient transmitted acoustic energy is present in the ROI to destroy the contrast agent. Accordingly, echo return 106' exhibits a substantially broader bandwidth (as a result of the contrast agent destruction) that extends into filter bandwidth region 110.

Note that by restricting the bandwidth of the transmit RF acoustic signals 100–106, the bandwidth of the tissue second harmonic response is largely restricted to regions outside of filter bandwidth region 110. However, due to the substantial spreading of the echo energy when destruction of the contrast agent occurs, the echo energy within bandwidth 110, is substantially that from the contrast agent. It is that signal energy that is then used to produce physiologic images.

Returning to FIG. 1, once all lines of a scan, at least within an ROI, have been processed by filter procedure 35, the resulting frame is stored in frames memory portion 37 of RAM 36. Control procedure 32 then transfers the resulting frame to scan converter 38 where the data is converted to a raster image and is then passed to video controller 40 which causes the image to be shown on display 24. Accordingly, the resulting image is derived from signal energy that falls within filter bandwidth 110, such signal energy mainly being the returns from contrast agent during a destruction event. The image is thus not burdened with tissue second harmonic response signal energy and improved image contrast is the result.

As an example, if a transmit waveform of six cycles of a sine wave at 1.8 MHz is used, the tissue echo response occurs at 1.8 MHz and at 3.6 MHz (as well as at higher harmonics but at substantially reduced magnitudes). Relatively little tissue response is seen at 2.7 MHz. Thus filter bandwidth 110 can be centered at 2.7 MHz (i.e., 1.5 times the transmit frequency) with a bandwidth of 0.5 MHz, to selectively pass the echo response signals that result from the contrast agent. The receiving filter bandwidth may also be set at 2.5 or 0.5 times the transmit frequency.

When the ROI is being imaged it may, and probably will, be moving during the procedure of the invention. To avoid introducing movement artifacts into the image, an ECG signal 59 is fed to CPU 30 which uses that signal to synchronize the times at which the transmit events are initiated from transducer 12. This enables a frame image to be derived for the ROI at a same relative time after each ECG signal and allows an accumulation of substantially identical images.

It should be understood that the foregoing description is only illustrative of the invention. Various alternatives and modifications can be devised by those skilled in the art without departing from the invention. For example, while the procedures required to perform the method of the invention have been described as being already loaded into RAM or present in ROM, they may be stored on a memory device 31 (FIG. 1) and loaded on an as-needed basis. Accordingly, the present invention is intended to embrace all such alternatives, modifications and variances which fall within the scope of the appended claims. Additionally, the technique can be combined with other techniques used to enhance the detection ration of contrast agents.

What is claimed is:

1. An ultrasound system for imaging a microbubble contrast agent in a region of fluid flow or tissue perfused with blood or other fluid, said system comprising:

transducer means for transmitting ultrasound signals having a fundamental frequency f at a sufficient power level to destroy said microbubble contrast agent to produce echo signals having a greater bandwidth and a lower amplitude than the transmitted ultrasound signals and for receiving said echo signals resulting from interaction of said ultrasound signals with both tissue and said microbubbles;

receiver means for receiving said echo signals and for selectively extracting signal components therefrom comprising one or more frequency bands located between integer multiples of said frequency f; and computation means for producing images principally from signal components falling within said one or more frequency bands located between integer multiples of said frequency f, wherein said frequency f is 1.3 MHz, said one or more frequency bands located between integer multiples of said frequency f is 3.6 MHz and said receiver means extracts signals having a bandwidth of about 0.8 MHz, centered at 3,6 MHz.

2. A method for controlling an ultrasound system to image a microbubble contrast agent in a region of fluid flow or tissue perfused with blood or other fluid, said method comprising the steps of:

a) receiving echo signals resulting from interaction of ultrasound signals with said microbubbles, said ultrasound signals transmitted at a fundamental frequency f at a sufficient power level to destroy said microbubble contrast agent and to produce said echo signals having a greater bandwidth and a lower amplitude than the transmitted ultrasound signals;

b) selectively extracting signal components from the received echo signals comprising one or more frequency bands located between integer multiples of said frequency f; and c) producing images principally from said signal components extracted from said one or more frequency bands located between integer multiples of said frequency f, wherein said frequency f is 1.3 MHz, said one or more frequency bands located between integer multiples of said frequency f is 3.6 MHz and step d) extracts signals having a bandwidth of about 0.8 MHz, centered at 3,6 MHz.

3. A memory media including instructions for controlling an ultrasound system to image a microbubble contrast agent in a region of fluid flow, or tissue perfused with blood or other fluid, said memory media comprising:

a) means for controlling said ultrasound system to transmit ultrasound signals having a fundamental frequency f at a sufficient power level to destroy said microbubble contrast agent to produce echo signals having a greater bandwidth and a lower amplitude than the transmitted ultrasound signals and for receiving said echo signals resulting from interaction of said ultrasound signals with said microbubbles;

b) means for controlling said ultrasound system to selectively extract signal components from the received echo signals comprising one or more frequency bands located between integer multiples of said frequency f; and c) means for controlling said ultrasound system to produce images principally from said signal components extracted from said one or more frequency bands located between integer multiples of said frequency f, wherein said frequency f is 1.3 MHz, said one or more frequency bands located between integer multiples of said frequency f is 3.6 MHz and said receiver means extracts signals having a bandwidth of about 0.8 MHz, centered at 3.6 MHz.

* * * * *

UNITED STATES PATENT AND TRADEMARK OFFICE
CERTIFICATE OF CORRECTION

PATENT NO. : 6,533,727 B1
DATED : March 18, 2003
INVENTOR(S) : George A Brock-Fisher It is certified that error appears in the above-identified patent and that said Letters Patent is hereby corrected as shown below:

<u>Title page,</u>
Item [73], Assignee, change "Phillips" to -- Philips --.

Signed and Sealed this

Sixteenth Day of September, 2003

JAMES E. ROGAN
*Director of the United States Patent and Trademark Office*